United States Patent [19]
Greff et al.

[11] Patent Number: 6,102,205
[45] Date of Patent: Aug. 15, 2000

[54] PREPOLYMER COMPOSITIONS COMPRISING AN ANTIMICROBIAL AGENT

[75] Inventors: Richard J. Greff, St. Pete Beach, Fla.; Ian N. Askill, Colorado Springs, Colo.

[73] Assignee: MedLogic Global Corporation, Colorado Springs, Colo.

[21] Appl. No.: 08/947,109

[22] Filed: Oct. 8, 1997

[51] Int. Cl.$^7$ .......................... A61B 17/06; A61K 31/79; A61L 25/00
[52] U.S. Cl. ......................................... 206/438; 424/78.25
[58] Field of Search .......................... 424/78.25; 206/438

[56] References Cited

U.S. PATENT DOCUMENTS

| | | | |
|---|---|---|---|
| 4,156,067 | 5/1979 | Gould | 424/78.25 |
| 4,197,318 | 4/1980 | Sipos | 424/78.25 |
| 4,479,933 | 10/1984 | Akimoua et al. | 424/78.35 |
| 4,584,192 | 4/1986 | Dell et al. | 424/78.25 |
| 5,302,392 | 4/1994 | Karakelle et al. | 424/78.25 |

FOREIGN PATENT DOCUMENTS

| | | | |
|---|---|---|---|
| 2557607 | 7/1976 | Germany | 424/78.25 |
| 451717 | 3/1975 | U.S.S.R. | 424/78.25 |

*Primary Examiner*—Peter F. Kulkosky
*Attorney, Agent, or Firm*—Burns, Doane, Swecker & Mathis LLP

[57] ABSTRACT

Disclosed are biocompatible prepolymer compositions comprising a compatible antimicrobial agent and, in particular, a compatible iodine containing antimicrobial agent. These compositions provide for in situ formation of an antimicrobial polymeric film on mammalian skin.

16 Claims, No Drawings

PREPOLYMER COMPOSITIONS COMPRISING AN ANTIMICROBIAL AGENT

BACKGROUND OF THE INVENTION

1. Field of the Invention

This invention is directed to prepolymer compositions comprising a compatible antimicrobial agent and, in particular, an iodine containing antimicrobial agent. These compositions provide for in situ formation of antimicrobial polymeric films on mammalian skin which films are useful as wound dressings, wound bandages, surgical incise drapes, wound closure materials which replace or are an adjunct to sutures, and the like.

This invention is also directed to kits of parts comprising such prepolymer compositions and an applicator means for applying the composition to mammalian skin.

REFERENCES

The following publications, patent applications and patents are cited in this application as superscript numbers:

[1] Hawkins, et al., Surgical Adhesive Compositions, U.S. Pat. No. 3,591,676, issued Jul. 6, 1971
[2] Halpern, et al., Adhesive for Living Tissue, U.S. Pat. No. 3,667,472, issued Jun. 6, 1972
[3] Blum, et al., In vitro Determination of the Antimicrobial Properties of Two Cyanoacrylate Preparations, J. Dent. Res., 54(3):500–503 (1975)
[4] Barley, et al., Methods for Treating Non-Suturable Wounds by Use of Cyanoacrylate Adhesives, International Patent Application Publication No. WO 93/25196, published Dec. 23, 1993
[5] Barley, et al., Methods for Treating Suturable Wounds by Use of Sutures and Cyanoacrylate Adhesives, U.S. Pat. No. 5,254,132, issued Oct. 19, 1993
[6] Khan, et al., "Preparation of a Skin Surface for a Surgical Procedure", U.S. Pat. No. 5,547,662, issued Aug. 20, 1996
[7] Byram, et al., Methods to Inhibit Acute Radiation Induced Skin Damage, International Patent Application Publication No. WO 96/34610, published Nov. 7, 1996.
[8] Cardarelli, et al., "Film Forming Antimicrobial Material", U.S. Pat. No. 4,374,126, issued Feb. 15, 1983
[9] Barnes, "Biocidal Complex and Dressing Formed Therefrom", U.S. Pat. No. 5,051,256, issued Sep. 24, 1991
[10] Dell, "Film-Forming Composition Containing an Antimicrobial Agent and Methods", U.S. Pat. No. 4,542,012, issued Sep. 17, 1985
[11] Askill, et al., "Methods for Draping Surgical Incision Sites Using a Biocompatible Prepolymer", U.S. patent application Ser. No. 08/941,094, filed concurrently herewith as Attorney Docket No. 026446-108
[12] Brink, et al., "Film-Forming Emulsion Containing Iodine and Methods of Use", U.S. Pat. No. 5,173,291, issued Dec. 22, 1992
[13] Hagen, et al., "A Comparison of Two Skin Preps Used in Cardiac Surgical Procedures", AORN Journal, 62(3):393–402 (1995)
[14] Ritter, et al., "Retrospective Evaluation of an Iodophor-Incorporated Antimicrobial Plastic Adhesive Wound Drape", Clinical Orthopedics and Related Research, pp. 307–308 (1988)
[15] Osuna, et al., "Comparison of an Antimicrobial Adhesive Drape and Povidone-Iodine Preoperative Skin Preparation in Dogs", Veterinary Surgery, 21(6):458–462 (1992)
[16] Matsumoto, Chapter 3: Bacteriology and Wound Healing, in "Tissue Adhesives in Surgery", Medical Examination Publishing Company, Inc., Flushing, N.Y., USA, pp. 106–113 (1972)
[17] Beller, et al., Process for the Preparation of Iodine-Polyvinylpyrrolidone by Dry Mixing, U.S. Pat. No. 2,706,701, issued Apr. 19, 1955
[18] Hosmer, Process of Stabilizing Polyvinylpyrrolidone, U.S. Pat. No. 2,826,532, issued Mar. 11, 1958
[19] Siggin, Preparation of Iodine Polyvinylpyrrolidone Adducts, U.S. Pat. No. 2,900,305, issued Aug. 18, 1958
[20] Modern Plastics Encyclopedia, 1997
[21] Mixon, Surgical Drape having Incorporated therein a Broad Spectrum Antimicrobial Agent, U.S. Pat. No. 5,069,907, issued Dec. 3, 1991

All of the above publications, patent applications and patents are herein incorporated by reference in their entirety to the same extent as if each individual publication, patent application or patent was specifically and individually indicated to be incorporated by reference in its entirety.

STATE OF THE ART

Biocompatible prepolymer compositions, such as compositions comprising cyanoacrylate esters, have been disclosed for a variety of topical uses on mammalian skin including use as a replacement or adjunct for sutures or staples in closing the dermal layer of an incision after surgery.[1,2,5] Other disclosed topical uses of such prepolymer compositions include inhibition of acute radiation-induced skin damage[7] as well as in the in situ formation of a surgical incise drape.[11]

In each case, when topically applied to mammalian skin, the biocompatible prepolymer composition polymerizes to form a coherent polymeric film which adheres to the skin.

Notwithstanding the beneficial properties associated with such prepolymer compositions and their suitability for topical applications, these compositions do not possess a sufficiently broad spectrum of antimicrobial activity including activity against microbial spores and, accordingly, cannot assure reductions in microbial populations on mammalian skin surface either under or adjacent the polymeric film formed in situ on the skin.[3,6]

Many of the uses of prepolymer compositions enumerated above would, however, significantly benefit by a broad spectrum of antimicrobial property in the polymer film. For instance, when used as a surgical (incise) drape, such films would reduce microbial populations under and adjacent the drape including those at the incision site and, accordingly, would reduce the risk of post-operative infection. Such is the basic premise of commercial surgical drapes containing an antimicrobial agent impregnated directly into the drape or in an adhesive layer attached thereto where it was hoped that this agent would be released onto the skin surface to inhibit microbial growth.[13,14] Osuna, et al.[15] report, however, that when the antimicrobial agent is incorporated into the adhesive layer, the adhesive does not release sufficient amounts of the impregnated agent to be, by itself, antimicrobial. Without being limited to any theory, it is believed that the antimicrobial agent is too strongly bound onto/into the adhesive to be released onto the skin and/or that there is insufficient skin surface contact between the adhesive and the skin to effect release of a sufficient amount of antimicrobial agent.

As noted above, most prepolymer compositions do not possess broad antimicrobial activity and, accordingly, in situ formation of a polymeric film on mammalian skin which film possesses broad antimicrobial properties necessitates, of course, that an antimicrobially effective amount of a broad spectrum antimicrobial agent be incorporated into the prepolymer composition and that sufficient amounts of this agent be released from the polymeric film onto the skin to achieve an antimicrobial effect. The incorporation of such an antimicrobial agent into the composition is problematic at best because several disparate criteria must be simultaneously met. First, the antimicrobial agent must be soluble or dispersible in the prepolymer composition at the concentrations necessary to effect antimicrobial properties. Second, the antimicrobial agent employed must not cause premature polymerization of the prepolymer composition. Third, the antimicrobial agent employed must not prevent in situ polymerization of the prepolymer composition when applied to the skin. Fourth, the antimicrobial agent must be compatible with the intended use of the polymeric film by not inhibiting formation of a flexible, durable film. Fifth, the impregnated antimicrobial agent must be released from the polymerized film in situ on the patient's skin in sufficient amounts to be antimicrobial.

Because of these disparate properties, many conventional antimicrobial agents are unsuitable for use in the prepolymer compositions of this invention and typically an antimicrobial agent has been incorporated into a solution or emulsion of the formed polymer or into a polymer melt[21] and this solution or emulsion is then applied to the patient's skin. In such cases, subsequent evaporation of the solvent leaves a polymer film on the skin which film is permeated with the antimicrobial agent.[8,10,12] Since the polymer is preformed prior to application to the skin, these solutions/emulsions reduce the effective adherence of the polymer film to the skin and, accordingly, could lead to premature lifting or removal of the film from the skin. Moreover, the use of water and other solvents in the emulsion or solution leads to slow drying times for the film with the concurrent difficulty in determining when or if the solvent has evaporated sufficiently to provide a polymer film on the patient's skin.[6] Replacement of water in such aqueous formulations with a quick drying organic solvent such as acetone, isopropanol, etc. leads to noxious/flammable vapors in the operating room and, in many cases, these solvents cause skin irritation. In any event, the use of such emulsions or solutions requires application of relatively large quantities of these compositions onto the skin in order to account for the portion which evaporates therefrom.

Still, in another alternative, commercially available embodiment (e.g., IOBAN™), a polymeric film is coated with an adhesive layer having an antimicrobial agent incorporated into the adhesive. Such films, however, suffer from poor contact of the adhesive layer with the skin and subsequently reduced antimicrobial effects. Additionally, notwithstanding the use of the adhesive, the polymeric film can lift during surgical procedures which has an adverse effect on infection rates.[15]

In view of the clear benefits associated with the incorporation of an antimicrobial agent directly into the prepolymer composition, there is an ongoing need to formulate a prepolymer composition comprising a broad spectrum antimicrobial agent.

SUMMARY OF THE INVENTION

This invention is directed to prepolymer compositions comprising a polymerizable biocompatible prepolymer composition and an antimicrobially effective amount of a complex of iodine with a biocompatible polymer. These compositions provide for in situ formation of an antimicrobial polymeric film on mammalian skin. The specific antimicrobial iodine complex employed is compatible with the prepolymer composition insofar as the antimicrobial complex neither causes premature polymerization nor prevents polymerization of the monomer, rather a flexible, adhesive and durable polymer film is formed in situ on mammalian skin by this composition. Moreover, the antimicrobial agent is expected to be released from the polymeric film in antimicrobially effective amounts thereby imparting antimicrobial properties to the polymeric film.

Accordingly, in one of its composition aspects, this invention is directed to an antimicrobial prepolymer composition which comprises:

(a) a polymerizable biocompatible prepolymer composition; and (b) an antimicrobially effective amount of a complex of iodine molecules with a biocompatible polymer with the proviso that the biocompatible prepolymer composition is neither a cyanoacrylate prepolymer composition nor a silicone prepolymer composition.

Preferably, the polymerizable biocompatible prepolymer composition is selected from the group of prepolymers consisting of urethane acrylate, ($C_{1-C6}$ alkyl) methacrylate, ($C_1$–$C_6$ alkyl) acrylate, ($C_1$–$C_6$ hydroxyalkyl) acrylate, ($C_1$–$C_6$ hydroxyalkyl) alkacrylate, styrene, α-methyl styrene, vinyl acetate, one and two component epoxy materials, mixtures thereof, and the like.

Antimicrobial complexes of iodine molecules with a biocompatible polymer preferably include iodine complexes of polyvinylpyrrolidone polymers which are also referred to under the common name of Povidone Iodine or PVP-$I_2$ (commercially available from BASF, Mt. Olive, N.J., USA), as well as iodine complexes with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone[9] and the like. Preferably, the iodine containing polymer is Povidone Iodine which is commercially available from a number of sources.

The antimicrobial prepolymer compositions preferably further comprise an effective amount of a polymerization inhibitor, a biocompatible plasticizer, and a polymerization initiator.

This invention is also directed to a kit of parts useful for applying the antimicrobial prepolymer compositions described herein onto mammalian skin. In particular, such a kit of parts comprises (a) a container comprising therein an antimicrobial prepolymer composition as described above and (b) an applicator means for applying the composition onto mammalian skin.

DETAILED DESCRIPTION OF THE PREFERRED EMBODIMENTS

This invention is directed, in part, to biocompatible prepolymer compositions comprising a polymerizable biocompatible prepolymer and an antimicrobially effective amount of a compatible iodine containing antimicrobial agent. However, prior to discussing this invention in further detail, the following terms will first be defined.

Definitions

As used herein, the following terms have the following meanings:

The term "polymerizable biocompatible prepolymer compositions" refer to polymerizable monomers, oligomers or mixtures thereof including single or multi-component systems. The prepolymer composition will polymerize in situ on mammalian skin to form an adherent, water-insoluble polymeric layer over the skin. The prepolymer and resulting polymeric film are biocompatible with the skin as measured by the lack of moderate to severe skin irritation and the resulting polymer film is substantially non-toxic and can be removed from the skin by conventional means, e.g., sloughing off with the epidermal layer of the skin.

Included within the term "polymerizable biocompatible prepolymer compositions" are both single and multi-component systems. Single component prepolymer compositions include those wherein a single prepolymer is capable of polymerizing under suitable polymerization conditions (e.g., free radical conditions) to provide for a polymer film on mammalian skin. Such single component systems include well known reactive vinyl groups which form a biocompatible polymer such as urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ hydroxyalkyl) alkacrylate, styrene, α-methyl styrene, vinyl acetate, and the like. Additionally, such single component systems can also comprise polymerization inhibitors, polymerization initiators, colorants, perfumes, etc.

Multi-component prepolymer compositions include those wherein two or more components are employed to co-react under suitable polymerization conditions to provide for a polymer film on mammalian skin. An example of a two component system is a diepoxide and a diamine specifically exemplified by bis-phenol A diglycidyl ether and ethylene diamine.

Preferred prepolymers for use in this invention include, by way of example only, urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ hydroxyalkyl) alkacrylate, styrene, α-methyl styrene, vinyl acetate, one and two component epoxy materials, mixtures thereof, and the like. Mixtures of such prepolymers can also be employed.

Specifically excluded from such prepolymers are cyanoacrylate prepolymers comprising an iodine containing antimicrobial agent which are described in commonly assigned U.S. patent application Ser. No. 08/912,681, filed on Aug. 18, 1997 which application is incorporated herein by reference in its entirety. Also excluded are silicone prepolymers.

The polymerizable biocompatible prepolymer compositions described herein polymerize on mammalian skin tissue without causing histotoxicity or cytotoxicity.

The term "a biocompatible polymer" refers to polymers which, as iodine complexes (adducts), are compatible with in vivo applications of the prepolymer compositions onto mammalian skin including human skin. Representative polymers include polyvinylpyrrolidone, copolymers comprising polyvinylpyrrolidone which are optionally crosslinked, and the like. Suitable copolymers include copolymers of polyvinylpyrrolidone and vinyl acetate or other vinyl compounds which copolymers are optionally crosslinked with a polyisocyanate. The molecular weight of these polymers is not critical with number average molecular weights ranging from about 10,000 to about 1,000,000 and preferably from 30,000 to 300,000.

The term "a complex of iodine molecules with a biocompatible polymer" refers to an antimicrobial complex formed by the addition of iodine ($I_2$) to the biocompatible polymer. Such complexes are well known in the art and the resulting complex typically comprises both available iodine and iodine anions. These complexes, on contact with mammalian skin, are antimicrobial apparently by providing for a source of antimicrobial iodine. In any event, such complexes are employed only as starting materials herein and, by themselves, do not form a part of this invention.

These complexes are sometimes referred to herein simply by the term "iodine/polymer complexes". Such iodine/polymer complexes are distinguished from antibiotics which are frequently naturally derived materials from either bacteria or fungi and whose mode of action is to interfere with bacterial processes resulting in bacterial death. Contrarily, the complexes used in this invention are indiscriminate in destroying any microbes including fungi, viruses and bacteria apparently by release of iodine into the microbes and, accordingly, are properly referred to as antimicrobial agents.

A preferred iodine/polymer complex for use in the compositions of this invention is a polyvinylpyrrolidone iodine complex which is described in, for example, U.S. Pat. Nos. 2,706,701, 2,826,532 and 2,900,305[17-19] as well as at pp. 1106–1107 of the Tenth Edition of the Merck Index, Published by Merck & Co., Rahway, N.J., USA (1983) the disclosures of which are incorporated herein by reference in their entirety. This complex is commercially available under the name "povidone-iodine" from BASF, Mt. Olive, N.J., USA.

It is contemplated that other anti-microbial agents could be employed in place of the iodine/polymer complex in the compositions of this invention. Such other anti-microbial agents include, by way of example, anti-microbial chlorhexidine salts (e.g., chlorhexidine gluconate), silver, silver complexes, silver salts (e.g., silver sulfadiazine), silver oxide and the like.

The term "biocompatible plasticizer" refers to any material which is soluble or dispersible in the prepolymer composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in Modern Plastics Encyclopedia, 1997, the disclosure of which is incorporated herein by reference in its entirety. Specific plasticizers include, by way of example only, citrate plasticizers, phthalate plasticizers, and the like.

The term "polymerization inhibitor" refers to well known free radical inhibitors of prepolymers including materials such as hindered phenols, hydroquinone, 4-methoxyphenol, amines and the like. The polymerization inhibitor is typically employed in amounts effective to inhibit polymerization of the prepolymer composition until application of the composition onto the mammalian skin and initiation of polymerization as herein described. Preferably, the polymerization inhibitor is employed from about 0.01 to about 0.1 weight percent based on the total weight of the composition.

The term "initiator" refers to those well known polymerization initiators which are typically incorporated into the composition to initiate polymerization of the prepolymer. Such initiators include, by way of example, thermal initiators, light activated (e.g., UV) initiators, and the like. Examples of thermal initiators include peresters, peroxycarbonates, peroxides, azonitrile compounds, and the like. Promoters or accelerators such as metal salts and amines may be used with the initiators. The specific thermal initiator is preferably selected to initiate polymerization of the prepolymer at ambient skin temperatures (e.g., ~35° C.) or slightly above with additional heating.

Examples of light activated initiators include benzoin alkyl ethers, benzophenone, Darocur 1173 (available from Ciba Geigy, Ardsley, N.Y., USA), camphorquinone, and the like.

Preferably, the initiator is a light activated initiator and, after application of the prepolymer composition to mammalian skin, a light source is passed over the skin to initiate polymerization. Even more preferably, the light activated initiator is biocompatible with the skin as measured by the lack of moderate to severe skin irritation.

The term "antimicrobial agent" refers to agents which destroy microbes (i.e., bacteria, fungi, viruses and microbial spores) thereby preventing their development and pathogenic action.

Compositions

This invention is based on the novel and unexpected discovery that the iodine/polymer complexes described herein are compatible with prepolymer compositions forming a composition which, upon polymerization, provides for an antimicrobial polymeric film. Compatibility is assessed by the fact that these complexes are dispersible in the prepolymer composition at antimicrobially effective concentrations and when so employed, do not cause premature polymerization of the prepolymer composition and do not prevent effective polymerization of the prepolymer composition when applied to mammalian skin. Moreover, the polymerizable prepolymer composition comprising such complexes forms a flexible, durable polymer film having the iodine complex incorporated therein which complex will release iodine in sufficient amounts to provide antimicrobial properties to the film.

The compositions of this invention are prepared by adding the iodine/polymer complex to the prepolymer composition. The iodine/polymer complex is preferably added as a solid composition (e.g., commercially available solid PVP-Iodine). Upon addition of the solid iodine/polymer complex to the prepolymer composition, the resulting system is thoroughly mixed to obtain a homogeneous suspension.

The amount of iodine/polymer complex added to the composition is a sufficient amount such that the resulting polymeric film is antimicrobial. Preferably, from about 10 to about 40 weight percent of the iodine/polymer complex and more preferably from about 10 to 25 weight percent is added to the composition based on the total weight of the composition.

The specific amount of iodine/polymer complex required to effect antimicrobial properties in the resulting polymeric film can be readily measured by conventional in vitro assays measuring zones of microbial growth inhibition around the film. Zones of inhibition of at least 1 millimeter and preferably 3 millimeters from the edge of the film when tested in the manner of Example 6 below evidence that the polymeric film is antimicrobial. Assessing the amount of iodine/polymer complex required in the polymeric film to effect such a zone of inhibition is well within the skill of the art.

The composition of the antimicrobial complex and the polymerizable biocompatible prepolymer can be formulated to a specific viscosity to meet disparate demands for the intended application of the composition. For example, relatively low viscosities are often preferred where application is to be made to a large surface area (e.g., abdominal surfaces). This preference results from the fact that these forms are less viscous and, accordingly, will permit more facile large surface area application of a thin film. Contrarily, where application is to be made to a specific position on the skin (e.g., elbow surfaces, knee surfaces and the like), higher viscosity materials are preferred to prevent "running" of the material to unintended locations.

Accordingly, these compositions have a viscosity of from about 2 to 50,000 centipoise at 20° C. For low viscosity applications, viscosity ranges of from about 2 to 1,500 centipoise at 20° C. are preferred. More preferably, the biocompatible prepolymer employed in the composition is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like, with PMMA being preferred. Fumed silica is particularly useful in producing a gel for topical application having a viscosity of from about 1500 to 50,000.

Thickening agents are deemed to be biocompatible if they are soluble or dispersible in the composition and are compatible with the skin as measured by the lack of moderate to severe skin irritation.

The prepolymer compositions of this invention can optionally include a biocompatible plasticizer and such plasticizers are preferably included from about 10 to 40 weight percent and more preferably from about 20 to 30 weight percent based on the weight of the composition absent the antimicrobial agent.

Additionally, the prepolymer compositions described herein preferably include a polymerization inhibitor and a polymerization initiator in effective amounts to provide for in situ polymerization on mammalian skin. For example, an effective amount of a polymerization inhibitor is preferably included in the composition to inhibit premature polymerization of the composition. Likewise, the polymerization initiator is included in the composition in effective amounts to initiate polymerization when the composition is placed under polymerization conditions (e.g., light). As above, such initiators include thermal initiators, light activated initiators and the like and in situ polymerization of the prepolymer composition on mammalian skin preferably occurs within 0.5 to 5 minutes.

The biocompatible prepolymer compositions may additionally contain one or more optional additives such as colorants, perfumes, rubber modifiers, modifying agents, etc. In practice, each of these optional additives should be both miscible and compatible with the prepolymer composition and the resulting polymer. Compatible additives are those that do not prevent the use of the prepolymers in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

When employed, each of these additives are incorporated into the composition and the resulting composition mixed until homogeneous.

Utility

The methods described herein are useful in forming in situ a broad spectrum antimicrobial adherent polymer film on the skin surface of a mammalian patient. Such mammalian patients preferably include humans as well as, for example, domestic animals exemplified by horses, cows, dogs, sheep, cats, etc. and any other mammalian species.

The polymer film finds particular utility in inhibiting microbial contamination thereunder and in the areas immediately adjacent thereto. Accordingly, such polymeric films can be used to topically cover small wounds on skin surfaces which wounds do not penetrate through the dermal layer of the skin as, for example, in the manner described in Barley, et al.[4].When so employed, the antimicrobial biocompatible prepolymer composition is applied over the wound. Upon polymerization, an antimicrobial polymeric film is formed over the wound which provides for broad spectrum antimicrobial properties at the wound surface while also preventing exogenous contaminants from entering the wound.

Additionally, the polymeric films formed from the antimicrobial prepolymer compositions described herein can also be used in the in situ formation of a surgical incise drape in the manner described by Askill, et al.[11]. When so employed, the in situ formed film adheres to the mammalian skin surface to provide for a surgical incise drape which does not lift during surgery and has broad spectrum antimicrobial properties.

In either case, an antimicrobial polymeric drape is formed over the selected site by applying a biocompatible prepolymer composition of this invention to the skin surface at the site. As noted above, this composition comprises polymerizable biocompatible monomers and/or reactive oligomers (prepolymers) which, upon application to the skin polymerizes in situ to form an antimicrobial biocompatible polymeric film.

When used as either a small wound covering or as a surgical incise drape, the antimicrobial polymeric film will only adhere to the skin for a period of about 1–4 days after which time it sloughs off. This occurs because the polymeric film adheres only to the uppermost portion of the epidermal layer which is continuously in the process of being sloughed off and replaced by the underlying cells. Accordingly, the antimicrobial polymeric film need not be removed after in situ formation. However, if immediate removal of the polymeric film is required, such can be removed with a suitable solvent.

Kits

In view of the many different uses for topical application onto mammalian skin, this invention also encompasses a kit of parts useful for applying the antimicrobial prepolymer compositions described herein onto mammalian skin. In particular, such a kit of parts comprises (a) a container comprising therein an antimicrobial biocompatible prepolymer composition as described above and (b) an applicator means for applying the composition onto mammalian skin.

The container comprises any compatible material which stores the prepolymer composition without degradation of the container or prematurely polymerizing the prepolymer. Such materials include, by way of example, inorganic materials such as glass (including amber glass), metals, ceramics, and the like as well as organic materials such as polyolefins including fluorinated polyolefins, and the like.

Suitable applicator means include brushes, rollers, aerosols, swabs, wipes, and the like.

In one embodiment, the container and applicator means are combined into a single article such as a brush affixed to the terminal portion of the container wherein means are employed to prevent premature release of the prepolymer composition. For example, the brush may be overlaid with a removable impermeable barrier. When application of the prepolymer composition is intended, the barrier is simply removed.

In another embodiment, the container and applicator means are separate articles designed to mate with each other. For example, the prepolymer composition could be stored in an amber vial sealed with a screw cap and the applicator means includes a screw mechanism which mates with a complimentary screw mechanism on the top of the vial. When application of the prepolymer composition is intended, the cap is removed from the vial and the applicator is attached.

In still another embodiment, the container itself comprises a two-component system which is useful with 2-component epoxy prepolymer systems wherein the first component is segregated from the other. For example, a diepoxide composition is added to one component of the container and a diamine added to the other. At the time of use, the components are then mixed to provide for a polymerizable prepolymer system.

The following examples illustrates certain embodiments of the invention but is not meant to limit the scope of the claims in any way.

EXAMPLES

In the examples below, all temperatures are in degrees celsius (unless otherwise indicated) and all percents are weight percent (also unless otherwise indicated) except for percent inhibition which is true mathematical percentage. Additionally, the following abbreviations have the following meanings. If an abbreviation is not defined, it has its generally accepted meaning.

CFU=colony forming units
$cm^2$=square centimeters
conc.=concentration
flex.=flexibility
dur.=durability
g=grams
min.=minutes
ml=milliliters
mm=millimeters
ppm=parts per million
PVP-$I_2$=polyvinylpyrrolidone iodine complex
SAB-DEX=Sabouraud Dextrose
TSA=trypticase soy agar

EXAMPLE 1

This example illustrates the preparation of a prepolymer composition comprising PVP-$I_2$ as the antimicrobial agent. In this example, ambient conditions were employed unless otherwise noted.

Specifically, a prepolymer composition of this invention was prepared by combining a diepoxide resin (45 weight percent based on the total weight of the composition, available under the tradename Master Mend resin (60 second cure) from Loctite Corporation, Rocky Hill, Conn., USA) with PVP-$I_2$ (10 weight percent based on the total weight of the composition, available from Aldrich Chemical Company, Milwaukee, Wis., USA). The resulting mixture was stirred until homogeneous. To this mixture was added a diamine hardener (45 weight percent based on the total weight of the composition, available under the tradename Master Mend epoxy hardener—60 second cure time, from Loctite Corporation, Rocky Hill, Conn., USA) which composition was then mixed until homogeneous to provide for an antimicrobial prepolymer composition of this invention.

EXAMPLE 2

This example illustrates in vitro application of a composition prepared similar to that of Example 1, except that the composition contains 47.5 weight percent of the diepoxide, 47.5 weight percent of the diamine hardener and 5 weight percent of the PVP-$I_2$ all based on the total weight of the composition.

Specifically, the above composition was applied to a Parafilm sheet and then spread to obtain a thin film of approximately 2–6 mm in thickness. The cure time and other observations were recorded and are set forth in Table I below:

TABLE I

| Cure Time | Film Area | Film formed | Flexibility of film | Adhesion of film |
|---|---|---|---|---|
| 3 min. | 6 cm² | YES | Very good | Very good |

The thickness of the film resulted in observable heat being generated during the exothermic polymerization reaction which was attributable to the thickness of the film and the large quantities of reagents in close proximity thereto.

EXAMPLE 3

This example illustrates a further in vitro application of the composition prepared similarly to that of Examples 1 and 2 to form a polymeric film. In this Example, the composition was prepared using 3.0012 g of Master Mend epoxy resin, 0.3071 g of PVP-$I_2$, and 3.0251 g of Master Mend epoxy hardener.

Specifically, the composition of this Example was then applied to a Parafilm sheet and then spread to obtain a thin film of less than 1 mm in thickness both for the applied film and cured film. The cure time and other observations were recorded and are set forth in Table II below:

TABLE II

| Cure Time | Film Area | Film formed | Flexibility of film | Adhesion of film |
|---|---|---|---|---|
| 5 min. | 25.5 cm² | YES | Very good | Very good |

In this example, no appreciable heat was noted during the polymerization reaction. This was attributed to the fact that a thin film was employed which did not result in high concentrations of reagents in a given volume.

Additionally, the cure time for the compositions of each of Examples 2 and 3 corresponds substantially to the cure time for a similar composition containing no PVP-$I_2$ and, accordingly, the PVP-$I_2$ is deemed compatible with this two component prepolymer composition.

EXAMPLE 4

This example illustrates in vivo application onto mammalian skin of a prepolymer composition similar to that of Example 2.

Specifically, following the procedure of Example 2 above, a two component antimicrobial prepolymer composition was prepared which composition contained PVP-$I_2$. Approximately 2 g of this composition was applied onto the upper arm of a human male subject using a flat metal blade to spread the mixture into a smooth, flat film. The brownish film cured tack-free in about 2 minutes with a slight warming sensation under the film. The film remained intact on the upper arm for about 36 hours including exposure to two showers and an ocean swim. During this time, there was some lifting along the edge of the film. After about 36 hours, the film came off the upper arm in a single piece, about 5 mils thick. The skin theretofore under the film was normal in appearance with no redness or irritation.

EXAMPLE 5

This example illustrates the preparation of another prepolymer composition of this invention which composition employed PVP-$I_2$ as the antimicrobial agent. In this example, ambient conditions were employed unless otherwise noted.

Specifically, camphorquinone (0.5130 g, available from Aldrich Chemical Company, Milwaukee, Wis., USA) was combined with trihexyl-O-acetylcitrate (20.1781 g, available from Aldrich Chemical Company, Milwaukee, Wis., USA). The resulting composition was mixed until the camphorquinone was dissolved. This composition is later referred to as "Composition A".

At this time, acrylate urethane prepolymer (78.0605 g, available under the tradename Loctite 3104 from Loctite Corporation, Rocky Hill, Conn., USA) was mixed with dimethylamino ethylacrylate (2.0036 g, available from Aldrich Chemical Company, Milwaukee, Wis., USA) and this mixture was then placed into a darkened room, the flask was covered with aluminum foil and a magnetic stirrer was added. This composition is later referred to as "Composition B".

Composition A was then added to Composition B in the darkened room with mixing until homogeneous to provide for "Composition C" which is a prepolymer composition lacking an antimicrobial agent.

A small portion (1–3 drops) of Composition C was placed between two sheets of parafilm and exposed to bright white light from a projector bulb. The curing time for this composition was then measured. This test was repeated 3 times and the composition provided a reproducible cure time of about 10–15 seconds.

To composition C was added PVP-$I_2$ (20.1510 g, available from Aldrich Chemical Company, Milwaukee, Wis.). The resulting mixture was stirred in the darkened room until homogeneous. Then 1–3 drops of the resulting composition were placed between two sheets of parafilm and cured as above. The curing time for this composition was then measured. This test was repeated for a total of 3 runs and the composition provided a reproducible cure time of about 4 minutes and 30 seconds.

The above data confirms that PVP-$I_2$ is compatible with this two component prepolymer composition insofar as the resulting prepolymer composition cured to provide for an antimicrobial polymeric film.

EXAMPLE 6

The following example illustrates how the antimicrobial effects of a polymeric film of this invention can be determined.

A. Preparation of the Inoculum

Specifically, the surfaces of two TSA plates, 100×15 mm, are inoculated with stock cultures (maintained on TSA slants) with the following microorganisms using a sterile inoculating loop: *Staphylococcus aureus* (ATCC No. 6538) and *Staphylococcus epidermidis* (ATCC No. 12228). The plates are incubated at 30° to 35° C. for 24 hours. The surfaces of two SAB-DEX agar plates are streaked with *Candida albicans* and incubated at 20–25° C. for 48 hours.

The cultures are harvested with sterile saline. Each culture suspension is collected in a sterile container and sufficient sterile saline is added to reduce the microbial count to obtain a working suspension of approximately $1\times10^8$ CFU's per ml.

The specific microorganisms recited above are selected for inclusion herein because they are common human skin pathogens (bacteria and fungus).

B. Inoculation of Plates

Each of the three test microorganisms is used to inoculate individual TSA plates by streaking them with sterile cotton tip applicators saturated with the appropriate suspension. The plates are allowed to dry.

C. Inhibition Study

Films of polymerized prepolymer comprising 0%, 10%, 15%, 20% or 30% iodine polyvinylpyrrolidone complex are formed on filter disks and then cut into approximately 11 to 13 mm² pieces. The pieces are placed in the center of the appropriate inoculated TSA plates. An untreated filter disk is cut into half, and one-half is placed in the center of the appropriate inoculated TSA plate and the other one-half is place in the center of non-inoculated TSA plates, to serve as a negative control. Two inoculated plates of each microorganism are also used as positive controls without the test article. These plates are then incubated for 3 days at 30° to 35° C. After incubation, the plates are removed and examined for any signs of microbial growth inhibition.

Zones of inhibition extending at least 1 millimeter from the PVP-I$_2$ films evidence that the PVP-I$_2$ is leaching from the film and imparting antimicrobial properties to the film.

From the foregoing description, various modifications and changes in the composition and method will occur to those skilled in the art. All such modifications coming within the scope of the appended claims are intended to be included therein.

What is claimed is:

1. An antimicrobial prepolymer composition which comprises:
   (a) a polymerizable biocompatible prepolymer which, in monomeric form, is selected from the group consisting of urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ hydroxyalkyl) alkacrylate, styrene, α-methyl styrene, vinyl acetate, one and two component epoxy materials and mixtures thereof; and
   (b) an antimicrobially effective amount of a complex of iodine molecules with a biocompatible polymer.

2. The composition according to claim 1 wherein the polymerizable biocompatible prepolymer is urethane acrylate.

3. The composition according to claim 1 wherein the polymerizable biocompatible prepolymer is a ($C_1$–$C_6$ alkyl) methacrylate.

4. The composition according to claim 1 wherein the polymerizable biocompatible prepolymer is ($C_1$–$C_6$ alkyl) acrylate.

5. The composition according to claim 1 wherein the polymerizable biocompatible prepolymer is a ($C_1$–$C_6$ hydroxyalkyl) acrylate.

6. The composition according to claim 1 wherein the polymerizable biocompatible prepolymer is ($C_1$–$C_6$ hydroxyalkyl) alkacrylate.

7. The composition according to claim 1 wherein the polymerizable biocompatible prepolymer is styrene.

8. The composition according to claim 1 wherein the polymerizable prepolymer is α-methyl styrene.

9. The composition according to claim 1 wherein the polymerizable prepolymer is vinyl acetate.

10. The composition according to claim 1 wherein the polymerizable prepolymer is selected from one and two component epoxy materials.

11. The composition according to claim 1 wherein said complex of iodine molecules with a biocompatible polymer is polyvinylpyrrolidone iodine.

12. The composition according to claim 1 which further comprises a biocompatible plasticizer.

13. The composition according to claim 1 which further comprises a polymerization inhibitor and a polymerization initiator.

14. A kit of parts comprising:
   (a) a container comprising therein an antimicrobial prepolymer composition which comprises a mixture of:
      (i) a polymerizable biocompatible prepolymer which, in monomeric form, is selected from the group consisting of urethane acrylate, ($C_1$–$C_6$ alkyl) methacrylate, ($C_1$–$C_6$ alkyl) acrylate, ($C_1$–$C_6$ hydroxyalkyl) acrylate, ($C_1$–$C_6$ Hydroxyalkyl) alkacrylate, styrene, α-methyl styrene, vinyl acetate, one and two component epoxy materials and mixtures thereof; and
      (ii) an antimicrobially effective amount of a complex of iodine molecules with a biocompatible polymer
   wherein said composition is capable of forming a film on mammalian skin surfaces and further wherein said container comprises a compatible material which stores the prepolymer composition without degradation of the container or prematurely polymerizing the prepolymer; and
   (b) an applicator means for applying the composition onto mammalian skin wherein said applicator means is either affixed to the container and forms a single article or is designed to mate with the container and the container and applicator means form separate articles.

15. A kit of parts according to claim 14 wherein the container and applicator means are combined into a single article.

16. A kit of parts according to claim 14 wherein the container and applicator means are separate articles.

* * * * *